United States Patent
Fröberg et al.

(10) Patent No.: US 6,944,507 B2
(45) Date of Patent: Sep. 13, 2005

(54) ELECTRODE FOR A MEDICAL IMPLANT

(75) Inventors: Paul Fröberg, Bromma (SE); Kenneth Dahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 407 days.

(21) Appl. No.: 10/203,949

(22) PCT Filed: Jan. 29, 2001

(86) PCT No.: PCT/SE01/00163

§ 371 (c)(1),
(2), (4) Date: Aug. 14, 2002

(87) PCT Pub. No.: WO01/60447

PCT Pub. Date: Aug. 23, 2001

(65) Prior Publication Data

US 2003/0014099 A1 Jan. 16, 2003

(30) Foreign Application Priority Data

Feb. 18, 2000 (SE) ................................ 0000548

(51) Int. Cl.[7] ................................................. A61N 1/05
(52) U.S. Cl. ...................................................... 607/126
(58) Field of Search ................................. 607/115–156

(56) References Cited

U.S. PATENT DOCUMENTS

| | | | |
|---|---|---|---|
| 4,106,512 A | 8/1978 | Bisping | |
| 4,301,815 A | * 11/1981 | Doring | ........................ 607/126 |
| 4,550,737 A | 11/1985 | Osypka | |
| 4,574,800 A | 3/1986 | Peers-Trevarton | |
| 5,324,325 A | 6/1994 | Moaddeb | |
| 5,423,884 A | 6/1995 | Nyman et al. | |
| 5,522,876 A | 6/1996 | Rusink | |
| 5,573,814 A | 11/1996 | Giele et al. | |

FOREIGN PATENT DOCUMENTS

| | | |
|---|---|---|
| WO | WO 96/19259 | 6/1996 |
| WO | WO 97/45158 | 12/1997 |
| WO | WO 98/20933 | 5/1998 |
| WO | WO 01/60447 | 8/2001 |

* cited by examiner

*Primary Examiner*—Scott M. Getzow
(74) *Attorney, Agent, or Firm*—Schiff Hardin LLP

(57) ABSTRACT

An electrode lead for a medical implant, such as a pacemaker, has a proximal end for connection to the implant and a distal end opposite thereto having an electrode and fixation structure for holding the distal end in place relative to surrounding tissue. A distal end part at the distal end has a tape ring shape, in the form of a truncated cone, and the fixation structure forms a helical thread around the distal end part. The height of the thread is such that the crest of the thread is located within an imaginary, second truncated cone that is coaxial with the distal end part. The crest of the thread is located within an imaginary cylinder that is coaxial with the cylindrical lead body and which has the same diameter as the lead body, this imaginary cylinder intersecting the imaginary, second truncated cone.

5 Claims, 2 Drawing Sheets

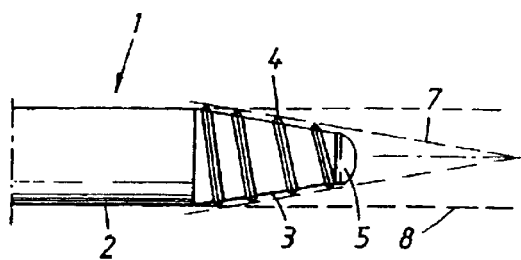
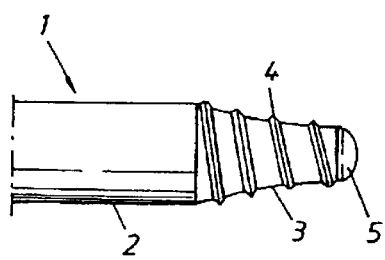
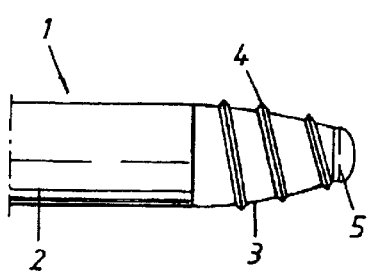
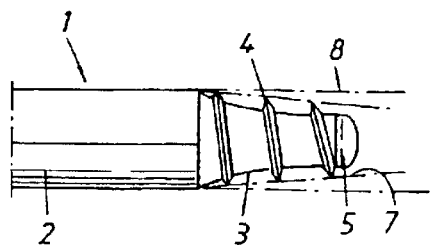

ELECTRODE FOR A MEDICAL IMPLANT

BACKGROUND OF THE INVENTION

1. Field of the Invention

The present invention relates to an electrode lead for an active implant, more particularly to a lead with electrodes for a pacemaker or similar device.

2. Description of the Prior Art

Modern pacemakers systems generally include an implantable pulse generator and one or several electrode leads connected to the pulse generator at the proximal end of the lead(s). The distal ends of the leads are provided with electrodes for electrical contact with the myocardium.

The pulse generator normally is implanted under the skin close to the shoulder of the patient and the leads are advanced through the subclavian vein and the vena cava for instance into the right atrium and/or the right ventricle of the heart. In order to hold the lead in place and to ensure that some or all electrodes on the lead are in contact with the myocardium, the distal end of the lead may be provided with tines or similar structures extending outwardly from the lead as for instance disclosed in PCT Application WO 98/20933. The tines or threads are for instance intended to engage the trabeculae in the apex of the ventricle.

There are several designs for facilitating the removal of leads provided with tines. One such design is disclosed in PCT Application WO 98/20933 in which the tines are designed so as to be detachable from the lead and remain attached to the trabeculae.

In other designs for attachment means for the distal end of the lead, the lead is provided with a helical thread extending laterally and outwardly from the lead, as disclosed in U.S. Pat. No. 4,550,737. The function of this design is generally similar to the function of the above design having tines as far as the function is concerned. The idea behind this design is to facilitate the insertion of the lead, particularly into the trabeculae. Retraction or explantation of the leads or any problems associated therewith is however not discussed.

U.S. Pat. No. 5,423,884 discloses a similar design to that disclosed in U.S. Pat. No. 4,550,737. This design also is provided with an external, helical thread on the outside of the lead. One embodiment thereof is designed with a helical, circumferential groove on the cylindrical outer periphery of the lead. Similar to the embodiment with the external thread, the groove is intended to facilitate the introduction of the lead into the veins and preferably is to be rotated during insertion by means of a motor. Again, retraction or explantation of the lead is not discussed.

SUMMARY OF THE INVENTION

An object of the present invention is to provide a lead with anchoring or fixation means that are simple in design and simple in use during both implantation and explantation.

DESCRIPTION OF THE DRAWINGS

FIG. 1 illustrates a first embodiment of the invention.

FIG. 2 shows a second embodiment of the invention.

FIG. 3 shows a variation of the embodiment in FIG. 2.

FIG. 4 relates to another embodiment of the invention.

DESCRIPTION OF THE PREFERRED EMBODIMENTS

Figure 5:
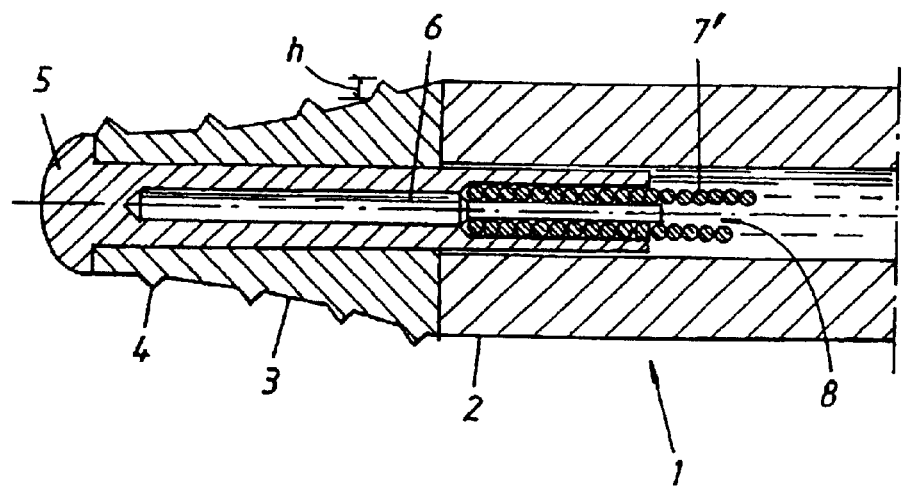
FIG. 5 is a longitudinal section through the embodiment in FIG. 2.

In the description below relating to the different drawings, parts that have the same function throughout all drawings will have the same reference numerals. For instance, the silicon sleeve on the lead body will have the same reference numeral 2, throughout all drawings.

FIG. 1 is a first embodiment of the distal end of a lead according to the invention. The lead itself is denoted 1 and is a standard lead with a tubular insulating silicon sleeve 2. The part 3 of the lead carrying the fixation structure 4 is in the form of a truncated cone with straight sides, the cone tapering in the distal direction. The small end of the cone carries a tip electrode 5 intended for contact with the myocardium. The lead 1 preferably has a diameter that is equal to the diameter of the large end of the conical part 3. The fixation structure 4 is in the shape of a circumferential thread located on the periphery of the conical part 3. The crest of the thread is located within the periphery of an imaginary second truncated cone 7 that is coaxial with the conical part 3 and within an imaginary cylinder 8 that is coaxial with the conical part 3 and that has a diameter being equal to the diameter of the large end of the conical part 3.

Other embodiments are shown in FIGS. 2 and 3. These embodiments differ from the embodiment in FIG. 1 in that the sides of the conical part 3 in FIG. 2 are slightly concave and in that the sides of the conical part 3 in FIG. 3 are slightly convex. The dimensions and shapes of the threads are however similar to the dimensions and threads in the embodiment according to FIG. 1. The crest of the threads consequently will be located on the periphery of a second imaginary truncated cone with slightly concave envelope surfaces respectively slightly convex envelope surfaces.

FIG. 4 illustrates an embodiment in which the thread 4 is located on a tapering conical part 3 and the height of the thread is allowed to vary progressively along the entire length of the conical part towards the distal and thereof. The crest of the thread 4 is, however, still located on the envelope surface of a second, imaginary truncated cone although this cone has a smaller top angle than the conical and part of the distal end of the lead.

It should be noted that the height of the thread may vary along the length of the thread as long as the condition that the crest of the thread is within the imaginary second cone is fulfilled. Thus the crest for instance could be located on a sinus curve in which the highest points would be located on the imaginary cone and the intermediate, lower parts would be located within the imaginary cone.

The details of the above designs are illustrated in FIG. 5, which is a longitudinal section through the embodiment in FIG. 2. The conical part 3 thus is provided with a fixation structure in the form of a continuous external helical thread 4 projecting from the body of the conical part. The height of the thread initially increases from zero to a predetermined height h in such a way that the crest of the thread touches the inside of an cylinder forming an extension of the outside of the tubular sleeve and which has a diameter that is equal to the diameter of the large end. From the point where the thread has the height h, the height is constant for the remainder of the thread. In this way the crest of the thread in this part will be located on the inside of a truncated cone that is concentric with the conical part 3. The pitch of the thread is chosen to be relatively large, i.e. such that a relatively small rotation of the tip would result in a relatively large longitudinal movement of the tip when unscrewing the same. The thread is continuous along its entire length.

The tip electrode 5 has an interior bore 6. A helical interior conductor 7 is inserted into a part of this bore and is thus electrically connected to the tip electrode 5. The bore 6 and the helical conductor 7 thus define an inner lumen 8 in the electrode lead for insertion of a guiding stylet.

For a standard lead with a diameter of about 3 mm, a suitable length of the conical part might be about 3 mm. The conical part can be made of a biocompatible polymer that may contain substances counteracting local traumas in the tissue. The conical part may also for instance be made of titanium made integrally formed with the tip electrode, in which case the threaded part would be electrically insulated by means of an electrically insulating coating.

To give an idea of the dimensions involved, the thread could for instance have a pitch corresponding to about 1–2 threads/mm with a crest angle about 90° and a maximal height of about 0.2–0.3 mm.

The implantation of the lead may be performed by means of an interior stylet engaging a recess (e.g. the interior bore 6) in the electrode so as to allow the transfer of a torque to the lead tip. An example of such a stylet is described in the published PCT Application WO 97/45158. A few turns of the lead and the lead tip will advance a few millimeters into the myocardium. In case the lead is to be anchored in the trabeculae, the rotation of the lead will advance the tip into the trabecular network without risking damage to the network due to the smooth edge of the thread. The number of turns necessary to secure the electrode would be approximately the same as the number of turns necessary to secure a normal, active, helical lead fixation means extending from the distal end of the lead of the type described in the published PCT Application WO 97/45158.

When the lead has been implanted for some time, a recess that is complementary to the tip may be formed around the tip in the surrounding tissue. The recess will have an interior thread that is complementary to the thread on the tip. When the lead is to be explanted, it is preferable to use a stylet that can be locked in the lead, i.e. a stylet having the capability of transferring both torque and a pulling force to the electrode. A stylet of this kind that could be used is for instance disclosed in U.S. Pat. No. 4,574,800. The stylet is inserted in the inner lumen of the lead and locked to the lead at the distal end thereof. Since the pitch of the thread is relatively large and the height of the thread is relatively small, the thread will come free from the complementary, interior threads formed in the recess in the tissue after a very slight rotation. The lead then easily can be pulled out from the tissue that has grown around the lead tip. Since no anchoring structure projects from the sides of the lead tip past the periphery of the cylindrical lead body, the lead also can be pulled easily through narrow passages around the intermediate parts of the lead, for instance in the veins.

Although modifications and changes may be suggested by those skilled in the art, it is the invention of the inventors to embody within the patent warranted heron all changes and modifications as reasonably and properly come within the scope of their contribution to the art.

What is claimed is:

1. An electrode lead for a medical implant, comprising:
    an elongated lead body having a proximal end adapted for connection to a medical implant and having a distal end opposite said proximal end;
    a distal end part located at said distal end, shaped as a truncated first cone and having a larger end;
    an electrode located at said distal end part and adapted for contact with surrounding tissue; and
    a fixation structure disposed on said distal end part and adapted for interaction with said tissue for holding said distal end in place relative to said tissue, said fixation structure comprising a helical thread proceeding around said distal end part and having a crest and a height so that said crest is disposed within an imaginary second cone coaxial with said distal end part, and said crest being disposed within an imaginary cylinder that is coaxial with said distal end part and which has a diameter equal to a diameter of said larger end of said distal end part, said cylinder intersecting said imaginary second cone.

2. An electrode lead as claimed in claim 1 wherein said distal end part has a smaller end spaced from said larger end, and a straight surface proceeding between said large end and said small end.

3. An electrode lead as claimed in claim 1 wherein said distal end part has a smaller end spaced from said larger end, and a concave surface proceeding between said large end and said small end.

4. An electrode lead as claimed in claim 1 wherein said distal end part has a smaller end spaced from said larger end, and a convex surface proceeding between said large end and said small end.

5. An electrode lead as claimed in claim 1 wherein said distal end of said elongated lead body has a distal tip, and wherein said height of said thread increases as said thread proceeds toward said distal tip.

* * * * *